United States Patent
Ruijters et al.

(10) Patent No.: US 8,681,935 B2
(45) Date of Patent: Mar. 25, 2014

(54) AUTOMATIC C-ARM VIEWING ANGLES FOR STRUCTURAL HEART DISEASE TREATMENT

(75) Inventors: Daniel Simon Anna Ruijters, Eindhoven (NL); Sander Denissen, Eindhoven (NL); Nicolaas Hylke Bakker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 36 days.

(21) Appl. No.: 13/388,214

(22) PCT Filed: Sep. 28, 2010

(86) PCT No.: PCT/IB2010/054365
§ 371 (c)(1),
(2), (4) Date: Jan. 31, 2012

(87) PCT Pub. No.: WO2011/042834
PCT Pub. Date: Apr. 14, 2011

(65) Prior Publication Data
US 2012/0183122 A1 Jul. 19, 2012

(30) Foreign Application Priority Data
Oct. 6, 2009 (EP) .................................. 09172362

(51) Int. Cl.
*G01N 23/04* (2006.01)
(52) U.S. Cl.
USPC .............................. 378/62; 378/205; 378/42
(58) Field of Classification Search
USPC .............. 378/42, 62, 205, 193, 196, 197, 198
See application file for complete search history.

(56) References Cited

U.S. PATENT DOCUMENTS

| 6,249,713 B1 * | 6/2001 | Geiger et al. ................ 700/57 |
| 6,256,037 B1 | 7/2001 | Callahan |

(Continued)

FOREIGN PATENT DOCUMENTS

| EP | 0972490 A1 | 1/2000 |
| EP | 1129663 A1 | 9/2001 |

OTHER PUBLICATIONS

Adrie C.M. Dumay et al, "Determination of Optimal Angiographic Viewing Angles: Basic Principles and Evaluation Study", IEEE Transactions on Medical Imaging, vol. 13, No. 1, Mar. 1994, pp. 13-24.

*Primary Examiner* — Hoon Song

(57) ABSTRACT

In a method for positioning an X-ray image acquisition device a straight reference plane (30) intersecting a three-dimensional representation of the object, a center point (34) within the intersection of the object, a normal vector (38) to the reference plane and at least one tangential vector (40) within the reference plane are created. Thereafter, the reference plane, the object's frame of reference and the X-ray image acquisition's frame of reference are registered. At least one viewing direction derived from the normal vector (38) and/or at least one tangential vector (40) is defined, wherein the X-ray image acquisition device is adjusted to the geometrical parameters of the X-ray image acquisition device. Thereby, planned and stored optimal viewing directions may be made available by a single push of a button, leading to automatically positioning of the X-ray image acquisition device and a much faster adjustment of the live guidance image, thus resulting in less exposure of radiation as well as a less cumbersome adjustment procedure. Furthermore a more optimal deployment of the interventional devices can be reached, since they can be more accurately positioned.

15 Claims, 5 Drawing Sheets

(56) References Cited

U.S. PATENT DOCUMENTS

| | | |
|---|---|---|
| 6,334,708 B1 | 1/2002 | Kosugi |
| 6,424,731 B1 | 7/2002 | Launay et al. |
| 2002/0006185 A1 | 1/2002 | Lienard et al. |
| 2002/0045817 A1 | 4/2002 | Ichihashi |
| 2004/0019264 A1 | 1/2004 | Suurmond et al. |
| 2008/0118126 A1 | 5/2008 | Sakaguchi |

* cited by examiner

AUTOMATIC C-ARM VIEWING ANGLES FOR STRUCTURAL HEART DISEASE TREATMENT

FIELD OF THE INVENTION

The invention relates to a method for positioning an X-ray image acquisition device, a medical viewing system comprising an X-ray image acquisition device and adapted for automatically positioning the X-ray image acquisition device, a computer program element for conducting the method for positioning an X-ray image acquisition device and a computer readable medium.

BACKGROUND OF THE INVENTION

Structural heart disease includes many conditions or diseases that may affect the heart muscle itself, the constitution of the heart and the heart valves that control the flow of blood in an out of the heart. Structural heart disorders may already be present at birth or they may develop later in life and can be caused by several conditions. For example, coronary artery diseases may cause blockages of the heart's arteries. It is common to conduct minimal invasive treatment in order to improve the heart condition. For example, insufficiency or stenosis of the heart valves, congestive heart failure and cardiomyopathy may be reduced by invasive treatment. These treatments may include angioplasty and stent placement, surgical repair and replacement of the mitral valve, heart surgery in general and revascularization. In the following it is focused on the minimal invasive treatment of structural heart defects through minimally invasive percutaneous access (e.g. catheterization or needle insertion), which is guided e.g. under C-arm fluoroscopy.

Thereby, a dynamic three-dimensional roadmap provides a live guidance through tortuous vasculature or another pathological anatomical structure in that an overlay of real-time two-dimensional fluoroscopy images and a three-dimensional reconstruction of the vessel tree is achieved. The two-dimensional image may be provided by an X-ray image acquisition device, e.g. of a type called C-arm. As a result, an image shows the advance of a guide wire, a catheter, stents, coils or needles on a single image in real-time and it improves visualization during complex interventions.

In order to match the acquired two-dimensional images with the three-dimensional representation of the dataset, the frame of reference of the X-ray image acquisition device, for example a C-arm X-ray system, and the frame of reference of the three-dimensional multi-modality data set need to be registered. The direct registration to the two-dimensional projective X-ray an image can be performed either manually, or automatically, employing a registration algorithm.

For the various purposes of interventional treatments an optimal direction of view is mandatory. This means, the surgeon or clinician must have the ability to watch each detail needed for a correct application of intracardiac devices or other instruments. Therefore, it is necessary to choose an appropriate viewing angle in order to be able to optimize the view for a clinician during the invasive procedure. It therefore is needed to adjust the X-ray imaging apparatus so that the desired viewing angle can be achieved.

For example, the major vessels of the coronary circulation are the left main coronary that divides into left anterior descending and circumflex branches, and the right main coronary artery. The left and right coronary arteries originate at the base of the aorta from openings called the coronary ostia located behind the aortic valve leaflets. During interventional treatments of the aorta, for example deployment of a stent, the clear visibility of the ostia is mandatory in order to prevent a blockage of the ostia by means of the stent to be deployed.

In U.S. Pat. No. 6,424,731 B1 a method for controlling an X-ray image acquisition device for enabling the device to automatically follow a viewing direction onto a three-dimensional representation of a vessel to be examined in real-time is disclosed. Further, this method allows prevention of collisions with a patient's body in that it allows prediction of geometry parameters that are physically not possible without collision.

Further, in US 2002/0006185 A1 a method for automatic positioning of an X-ray image acquisition device is disclosed, in which a first direction is determined, the viewing direction being calculated so that the image quality will be superior to hat would be obtained with a viewing direction parallel to the first direction.

SUMMARY OF THE INVENTION

As described above, selecting the most optimal viewing angle for an appropriate live image guidance is essential during interventional treatments. Hence, the geometrical parameters for the X-ray image acquisition device providing the two-dimensional fluoroscopy images have to be adapted for this purpose. It is common to use a C-arm type X-ray image acquisition device which means that the C-arm geometry has to be set accordingly. Usually, the C-arm geometry is adapted through manual control inputs on a user interface in order to follow the desired viewing direction which may be cumbersome during the invasive procedure. Also, adjusting the viewing direction during the intervention leads to an unnecessary exposure of the patient to X-ray radiation.

Furthermore, in adjusting viewing angles of an X-ray image acquisition device a parallax effect may be apparent. A parallax stands for the apparent displacement of an object viewed along two different lines of sight. It may be measured by an angle of inclination between these two lines. Objects situated nearby the viewer or the X-ray source, respectively, develop a larger parallax than more distant objects when they are observed from different positions. In nature, this parallax leads to the ability of humans or animals to determine a distance by viewing an object along two different lines of sight. Generally, since the fluoroscopy images are two-dimensional this parallax effect may influence the image quality regarding imprecise reproduction or representation of object lengths in the live images.

Hence, there may be a need for a method for positioning an X-ray image acquisition device in order to achieve an optimal viewing direction to a pathology to be monitored during an interventional treatment.

Also, there may be a need for a method for positioning an X-ray image acquisition device that allows selection of at least one optimal viewing angle for the pathological anatomical structure in a three-dimensional representation and an automatic adjustment of the X-ray image acquisition device to meet these desired viewing angles.

Furthermore, there may be a need for a method for positioning an X-ray image acquisition device that allows minimizing or completely eliminating the parallax effect of live fluoroscopy images.

These needs may be reached with a method for positioning an X-ray image acquisition device, a medical viewing system comprising an X-ray image acquisition device, a computer program element for conducting the method and a computer readable according to the independent claims.

Various exemplary and advantageous embodiments of the present invention are described in the dependent claims.

For the following description of the present invention it is assumed that a three-dimensional reconstruction of the pathological structure to be examined is present. Usually, this three-dimensional reconstruction is pre-operatively obtained through one or several methods well known for a person skilled in the art. This reconstruction may be realized on the basis of X-ray images acquired with a C-arm X-ray image acquisition device from several directions of view. Alternatively, a CT or MR scan or the such for diagnostic purposes and treatment planning may be used for this purpose. Nevertheless, the subject of the present invention is not limited to the type of acquiring a three-dimensional representation of a structure.

Assuming the visibility of the pathologic anatomical structure in the three-dimensional dataset, according to a first aspect the method according to the present invention is enabled to fit a straight plane through the pathological anatomical structure, which structure may be an aortic valve, a shunt etc. The plane is intersecting the pathological anatomical structure. This plane may further be referred to as the reference plane since chosen viewing directions are defined referring to this plane as described further below. A center point on this plane is then defined in the middle of the pathologic anatomical structure, e.g. the geometrical center of the intersection area between of the reference plane and the pathologic anatomical structure. The optimal viewing direction can then be defined relative to this reference plane and the center point inside the pathologic anatomical structure.

The optimal viewing direction may be defined in relation to the reference plane, which may be supported by the definition of a normal vector and a number of tangent vectors. The normal vector can be defined as a vector through the center point of the pathologic anatomical structure and extends perpendicularly to the plane. A tangent vector may be a vector through the center point, extending tangentially on the plane. In the latter case, the vector may be any vector on the plane that runs through the center point of the plane.

The basic idea of the method according to the present invention lies in the fact that deriving from a three-dimensional dataset one or more optimal viewing directions may be chosen prior to the interventional treatment. This may be conducted by consulting the three-dimensional representation of the pathologic anatomical structure on a screen of a separate calculating device or a calculation unit comprised in the X-ray image acquisition device. In rotating and/or translating this representation viewing directions considered best for the interventional treatment may be found. When more than one interventional treatment needs to be conducted various viewing directions may be chosen that all refer to the reference plane and the normal and tangential vectors. Furthermore, also more than one viewing direction may be stored to guide different aspects within a single treatment.

The advantage of defining the viewing direction relative to a reference plane by tangential vectors as X-ray image acquisition device viewing directions lies in the ability for precise placement of an intracardiac device, which may be realized as an aortic valve stent, inside the pathology location. Consequently, a viewing direction in normal direction, in the range of the normal vector on the reference plane may be useful for placing for example an atrial septal defect closure device or similar.

For example, the surgeon checks from the three-dimensional data set from which directions an optimal view onto the pathologic anatomical structure can be achieved when a stent needs to be deployed in an aorta. It is considered mandatory that this stent does not cover any ostia. Therefore, the surgeon may choose such a viewing direction in which the aorta and the ostia are clearly visible at all times when the stent is advanced in the aorta. The tangent vectors described earlier provide such an optimal viewing direction. Hence, it shall be ensured that no ostia is covered by any vessel. Resulting, the stent may be deployed ideally.

It is one aspect of the present invention to provide the ability to store these planned optimal viewing directions for the interventional treatment in a storage unit that is connected to a data processing unit comprised in the X-ray image acquisition device. Thereby it is possible to retrieve all optimal viewing directions by an appropriate command in the data processing unit.

The geometrical parameters of the X-ray image acquisition device, for example position and angle of X-ray radiation source and X-ray beam as well as the position and angle of X-ray detection module, may be controllable through the data processing unit or a separate control unit. Thereby it allows the X-ray image acquisition device to follow any selected optimal viewing direction automatically.

Before any optimal viewing direction may be used during the intervention, the relation between the planning frame of reference, which represents the optimal viewing direction, the frame of reference of the X-ray image acquisition device and the intra-operative patient space, which may depend on the patient's position on a table, has to be matched. This may be done through an automatic registration algorithm or through a manual registration process.

For example, the registration is performed through an automatic segmentation of the trachea in a three-dimensional data set, and manually determining the pose of the trachea with respect to two X-ray images, taking by the X-ray image acquisition device from different angles. Thereby, the three-dimensional dataset and the live two-dimensional fluoroscopy images are aligned with each other.

It is to be noted that this registration process is intrinsic if the three-dimensional data set used for planning was obtained peri-operatively by the X-ray image acquisition device.

By conducting a method according to the present invention comprising the above identified aspects several advantages may be achieved. A misplacement of a percutaneous device or other medical instruments can be prevented. By planning optimal viewing directions prior to the intervention an optimal viewing direction for the whole intervention procedure may be achieved. It should therefore be considered impossible to conduct the intervention with a sub-optimal viewing direction in which the surgeon may have a wrong assumption of the correct treatment, correct deployment of intracardiac devices or the such. Therefore, the method according to the present invention provides a clear improvement for interventional treatments.

Furthermore, conducting the method according to the present invention provides in a reduction of exposure of the patient's body to X-ray radiation. It may be unnecessary to adjust the X-ray image acquisition device several times during the interventional treatment where the live fluoroscopy images are not used for guiding the medical instruments. By the method according to the present invention an automatic adjustment of the X-ray image acquisition device provides for an optimal viewing direction at all times. Thereby, the intervention process is accelerated and thus the time of X-ray radiation exposure is reduced.

According to an advantageous embodiment of the present invention, the reference plane is fitted in the three-dimensional data set automatically. This may be conducted by expanding a plane in the pathology anatomical structure to be examined, wherein the average distance from all trajectory points to the plane is minimized.

In this context, it should be noted, that the pathology anatomical structure to be examined may be characterized by a pathology outline which is a closed trajectory through the three-dimensional space. For example for a shunt this is the minimal outline around the hole and for heart valves this is the minimal outline that contains the valve leaves. This outline may be determined by segmenting the pathology anatomical structure, so that an algorithm to fit a straight plane through this trajectory defined by the outline may be conducted.

Alternatively the plane may be set manually. This may be realized by a user through an appropriate input means connected to a graphical user interface displaying the three-dimensional representation of the pathology anatomical structure. The user may position a clip plane or indicate three three-dimensional points within the pathology anatomical structure that are sufficient for defining the spatial positions of a plane. For this purpose, the three-dimensional data set may be visible through a graphical user interface on a screen of the X-ray image acquisition device or a separate calculation unit connected to the X-ray image acquisition device or being adapted to store this information on a storage means. The three-dimensional representations may be rotatable and translatable.

In an advantageous embodiment of the present invention a center point is created on the reference plane, which center point may lie in the middle of the pathology anatomical structure. For example, a center point may be defined as a point on the plane that is close to the true center point which may be represented by a center of gravity of the area spanned by a pathology outline. It may be determined by averaging the coordinates of the pathology outline, or alternatively, it may also be set by the user via input means and a graphical user interface.

In a further preferred embodiment of the present invention the normal vector to the reference plane is determined. The normal vector extends perpendicularly from the reference plane and runs through the above defined center point.

Also, a set of tangential vectors is determined wherein tangential vectors are all placed directly on the plane and all extend through the center point.

Further on, the optimal viewing directions are derived from the normal vector and the set of tangent vectors. This means that for a chosen normal or tangent vector the viewing incidence of the X-ray system is such that the respective normalized normal or tangent vector is present in the set of normalized vectors running from the focal spot of the X-ray source to the X-ray detector.

In a preferred embodiment of the present invention the X-ray image acquisition device is automatically steered to a selected optimal viewing direction, accompanied by a subsequent adjustment of the three-dimensional representation and a registration. For example when the surgeon selects a stored optimal viewing direction on an appropriate user interface or the such the X-ray image acquisition device automatically moves to match this optimal viewing direction, the three-dimensional representation of the pathology anatomical structure is adjusted and both views are then registered in order to automatically adjust the live guidance view for the surgeon, preferably by a simple press on a button or by selecting a stored viewing direction on a touch screen or other input/output device.

In this context, the expression steering stands for adjusting the geometrical parameters of the X-ray image acquisition device such as position and angles of the X-ray detector, the X-ray radiation source, the X-ray radiation beam, etc., which highly depends on the type of X-ray image acquisition devices. It is common to use C-arm X-ray image acquisition devices which means that the steering process comprises adjusting at least three angles—rotation, angulation, L-arm—and may be the frame position of the C-arm within the operating room.

In a further preferred embodiment of the present invention the steering of the X-ray image acquisition device comprises the compensation of parallax errors. The parallax facts are thereby taken into account, which parallax effects are the consequence of the perspective in the X-ray image. Basically, the parallax compensation may be conducted as following by the example of a C-arm type X-ray image acquisition device. A focal spot of the detector source has a fixed distance from the iso-center of the C-arm geometry. A sphere with a radius set to this distance, around the iso-center describes all possible detector focal spot positions. As described above, the optimal view direction is defined in terms of a vector and the center point of the pathology. A straight line may be defined through this center point, in the direction of the optimal view vector. The intersection of this line and the previously described sphere, may determine the optimal position of the focal spot.

According to a further aspect of the present invention there is provided a medical viewing system, in particular a C-arm system or a computer tomography system. The medical viewing system comprises a data processing device adapted to conduct the above-described method steps.

According to a further aspect of the present invention there is provided a computer-readable medium on which there is stored a computer program for automatically positioning an X-ray image acquisition device. The computer program, when being executed by a data processor, is adapted for controlling exemplary embodiments of the above-described method.

According to a still further aspect of the present invention there is provided a computer program element for providing automatic positioning of an X-ray image acquisition device. The computer program element, when being executed by a data processor, is adapted for controlling exemplary embodiments of the above-described method.

The computer program element may be implemented as a computer-readable instruction code in any suitable programming language, such as, for example, JAVA, C++ and may be stored on a computer-readable medium (removable disk, volatile or non-volatile memory, embedded memory etc.). The instruction code is operable to program a computer or other programmable device to carry out the intended functions. The computer program may be available from a network, such as the World Wide Web, from which it may be downloaded.

Also, existing medical viewing systems may be upgraded with a new software, which, when being executed on a processor, causes the system to carry out the above-mentioned method steps according to the present invention.

It has to be noted that features and side effects of the present invention have been described with reference to different embodiments of the invention. However, a person skilled in the art will gather from the above and the following description that unless other notified in addition to any combination or features belonging to one embodiment also any combinations between features relating to different embodiments or to a manufacturing method is considered to be disclosed with this application.

The aspects defined above and further aspects of the present invention are apparent from the examples of embodiment to be described hereinafter and are explained with reference to the examples of embodiment. The invention will be described in more detail hereinafter for further explanation and better understanding of the present invention with reference to examples of embodiment but to which the invention is not limited. Identical or similar components in different figures are provided with identical reference numerals. The illustrations in the figures are schematic and are not to scale.

DETAILED DESCRIPTION OF EMBODIMENTS

Figure 1:
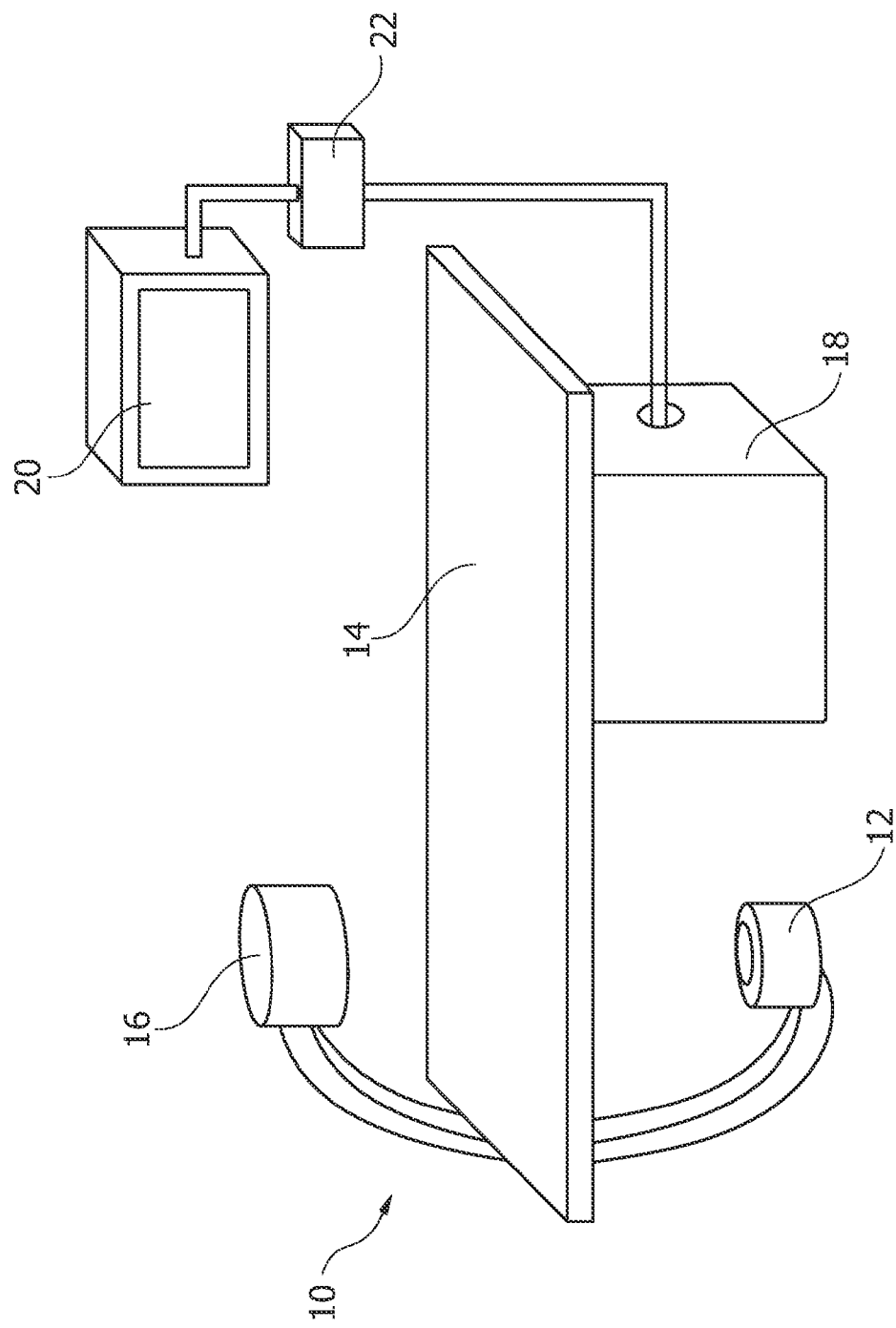
FIG. 1 shows an X-ray imaging system according to the present invention.

FIG. 1 schematically shows an X-ray imaging system 10 with a medical viewing system for automatically positioning of an X-ray image acquisition device.

The X-ray imaging system 10 comprises an X-ray image acquisition device with a source of X-ray radiation 12 provided to generate X-ray radiation. A table 14 is provided to receive an object to be examined. Further, an X-ray image detection module 16 is located opposite the source of X-ray radiation 12. During the radiation procedure, the examined object is located between the source of X-ray radiation 12 and the detection module 16. The latter sends data to a data processing unit or a calculation unit 18, which is connected to both the X-ray image detection module 16 and the X-ray radiation source 12. The calculation unit 18 is exemplarily located underneath the table 14 for saving space within the examination room. It is clear that it could also be located at a different place, such as in a different room or a different laboratory. Furthermore, a display unit 20 is arranged in the vicinity of the table 14 for displacing information to the person operating the X-ray imaging system, which can be a clinician such as a cardiologist or a cardiac surgeon. Preferably, the display unit 20 is movably mounted to allow for an individual adjustment depending on the examination situation. Also, an interface unit 22 is arranged to input information by the user.

Basically, the image detection module 16 generates images by exposing this subject to X-ray radiation, wherein said images are further processed in the calculation unit 18. It is noted that the example shown is of a so-called C-type X-ray image acquisition device. The X-ray image acquisition device comprises an arm in form of a C where the detection module 16 is arranged at one end of the C-arm and the source of X-ray radiation 12 is located at the opposite end of the C-arm. The C-arm is movably mounted and can be rotated around the object of interest located on the table 14. In other words, it is possible to acquire images with different directions of view.

The calculation unit 18 may be adapted to conduct the method according to the present invention and thus can be considered as or comprise the data processing device for automatically positioning the X-ray image acquisition device. Thereby, a data processor and preferably a storage means for storing the optimal viewing directions is provided as well as a related software that leads one program element for automatically position the X-ray image acquisition device, adapted for controlling exemplary embodiments of the above-described method. The software can be transferred into the calculation unit 18 by means of a computer-readable medium or through a network and may be realized as a complete new operating system or an update.

Figure 2A:
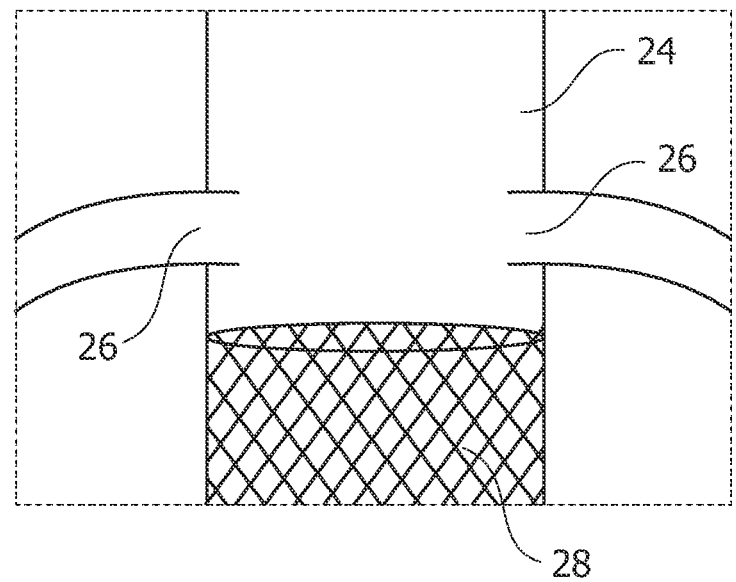
FIGS. 2a and 2b show a perpendicular view and an angulated view on an organ and a percutaneous device.

In FIG. 2a there is displayed an aorta 24 that comprises two ostias 26. During the interventional process, a stent 28 may be deployed on the aorta 24. As visible in FIG. 2a it has to be taken care, that the stent 28 does not cover the ostias 26. Therefore, a perpendicular viewing direction on the aorta 24, which means viewing directly perpendicular to the aorta's wall, can be considered an optimal viewing direction.

Figure 2B:
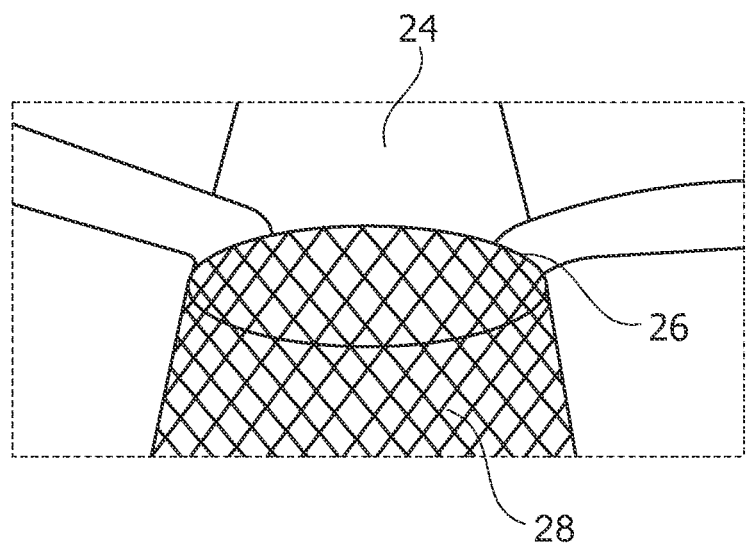

In FIG. 2b a slightly angulated viewing direction is presented on the same aorta 24 with two ostias 26. It is clear from the presentation in FIG. 2b that it is much harder to monitor the deployment of the stent 28 because the ostias 26 are not fully visible when the stent 28 is about to reach its final destination. Therefore, the direction of view in FIG. 2b can not be considered optimal because from this direction of view it is hard to prevent that the stent 28 covers the ostias. A surgeon has to assume whether the stent is deployed correctly or not and thus leads to an unwanted level of uncertainty.

Taking the example from FIGS. 2a and 2b it is explained, how a straight reference plane may be fitted to a pathology to be examined.

Figure 3:
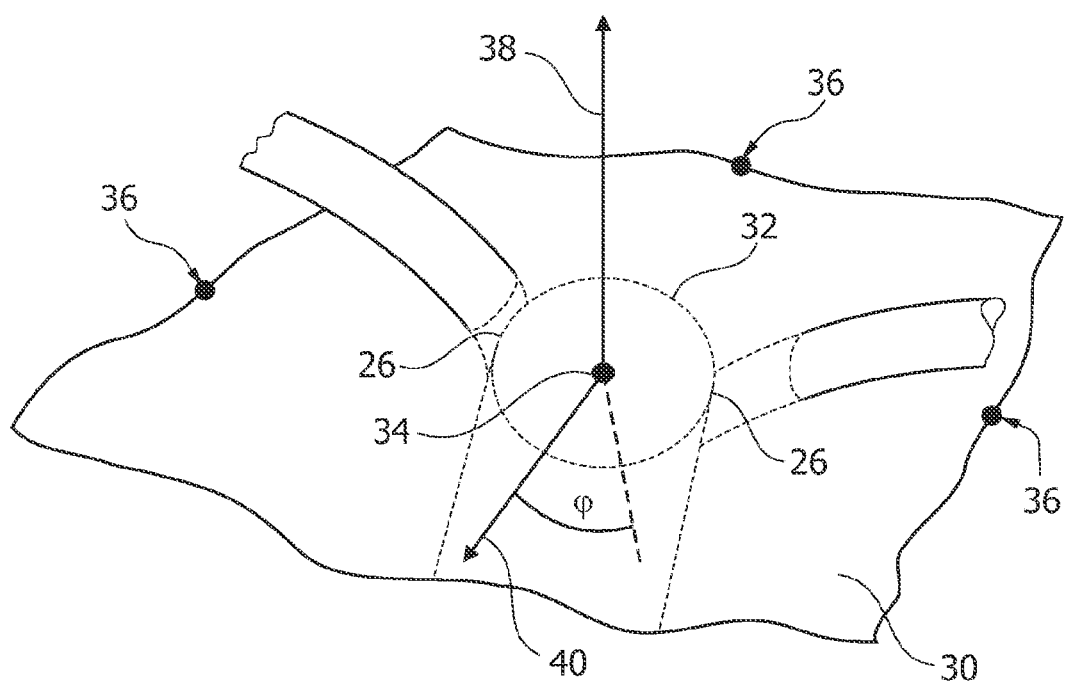
FIG. 3 shows a plane relative to a pathology to be examined.

In FIG. 3 the aorta 24 together with the ostias 26 is shown. According to the method of the present invention a plane 30 is fitted to an outline 32 of the pathology which is in this case the aorta 24 in the range of the two ostias 26.

The plane 30 is fitted in a way that minimal distances between all trajectory points of outline 32 and the plane 30 are realized. In order to receive the outline 32 a segmented sub-volume can be taken into consideration, wherein the segmentation may be generated automatically by methods known to a person skilled in the art. The outline 32 should be chosen such that e.g. an aorta area in a planar cross-section is minimal.

On plane 30 a center point 34 is created. This center point 34 may be determined as a geometrical center or center of gravity of an area limited by the outline 32. Alternatively, the surgeon may choose an own center point 34. Also, the surgeon may choose a plane 30 manually for example by defining three three-dimensional points 36 that span the plane 30 in a three-dimensional space.

On the center point 34 a normal vector 38 is created, that extends perpendicularly to the plane 30. Starting from the center point 34 a set of tangent vectors 40 are extending within the plane 30.

For the shown example a viewing direction parallel to a tangential vector 40 may be considered optimal, whereas in other cases (e.g. a shunt in the heart wall) a viewing direction parallel to the normal vector 38 may be considered optimal.

The optimal tangent direction may be chosen by rotating the three-dimensional representation of the pathology in order to find a viewing direction that is considered optimal.

A set of optimal directions of view may then be stored in a storage means and be made retrievable by an appropriate input with the user interface or an input means.

Figure 4:
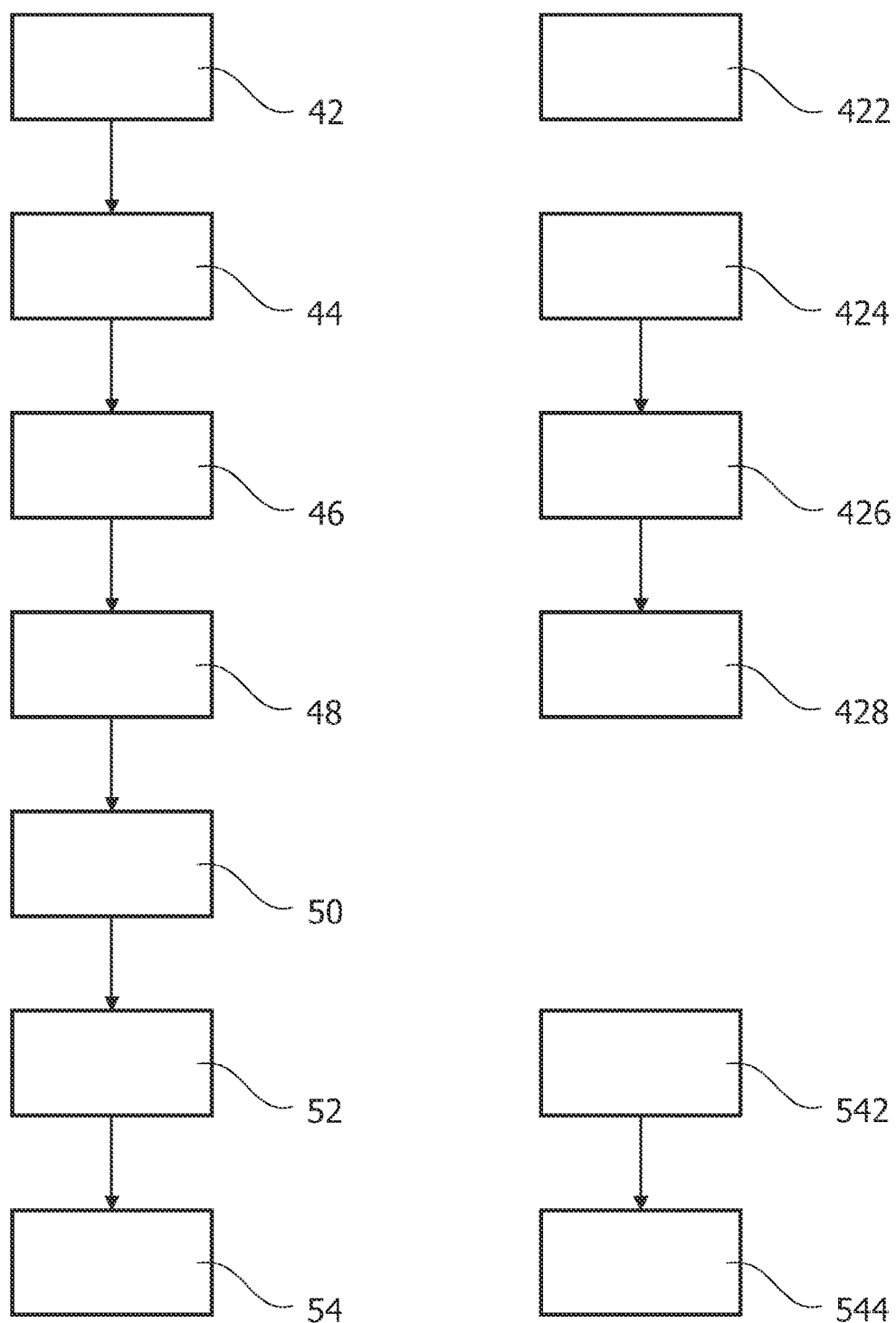
FIG. 4 shows a method according to the present invention.

In FIG. 4 the method according to the present invention is further described in detail. After defining/creating 42 a plane and defining/creating 44 a center point on the plane according to the outline 32 of the pathology to be examined optimal viewing directions may be found and then stored 46 in a storage means.

The creation of the reference plane 30 may comprises the feature of spanning 422 the reference plane such that average distance from trajectory points of the object to the reference plane are minimized.

Furthermore, the creation of the reference plane 30 may include segmenting 424 the object to be examined into sub-volumes, determining 426 an outline of a segmented sub-volume and spanning 428 the reference plane such that the average distance from the trajectory defined by the outline of at least one segmented sub-volume is minimized.

In order to match the acquired three-dimensional data set and the patient actually positioned on a table of the X-ray image acquisition device the planning and pathology space are registered 48.

During the intervention optimal viewing directions may be selected 50 to which the X-ray image acquisition device is steered 52 that can also be referred to as adjusting the geometry of the X-ray image acquisition device.

In order to prevent the length changes or errors in the viewing perspective a parallax compensation is conducted 54.

The parallax compensation may comprise the steps of generating 542 a sphere 58 around an iso-center 60 of the X-ray image acquisition device, wherein the radius of the sphere equals the distance between the center 60 of the X-ray image acquisition device and the X-ray radiation source 12, determining 544 an intersection between a straight line through the center point 60 of the reference plane 30 in the direction of the optimal viewing direction 56 and the sphere 58 and adjusting 52 the geometry parameters of the X-ray image acquisition device to match the intersection and a focal spot of the X-ray source.

Figure 5:
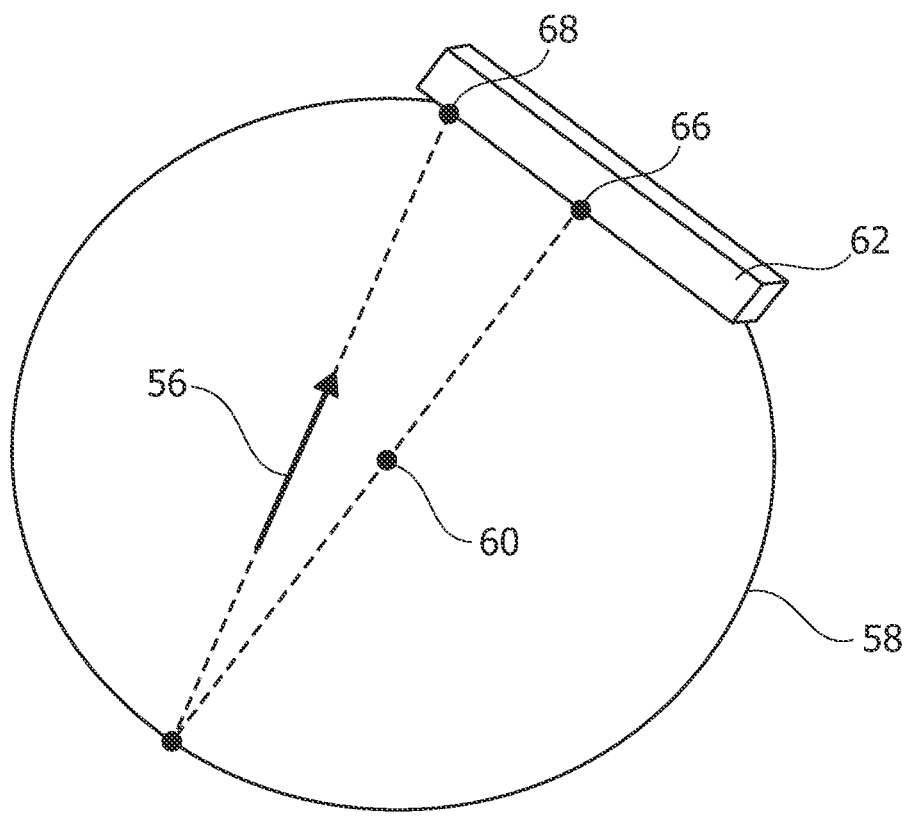
FIG. 5 demonstrates the parallax compensation schematically.

In FIG. 5 the parallax compensation is demonstrated schematically. A vector 56 defines an optimal viewing direction that reaches an X-ray detector 62, around which detector 62 a sphere 58 is constructed that resembles all possible focal spots of the X-ray source. The detector is not steered exactly into the direction of the desired viewing direction vector 56. Instead, the detector 62 is moved into a position that is directed to the intersection 64 of vector 56, the sphere 58 and a line extending from the center 66 of the detector 62 through an iso-center 60 of the sphere 58. Thereby, the optimal viewing direction vector 58 is projected as a point 68 onto the X-ray detector 62 and the parallax effect has been compensated appropriately.

By the method and a appropriate clinical workflow according to the present invention an efficient way to provide optimal viewing angle is achieved. From a three-dimensional data set the clinician or the surgeon may plan the intervention and is able to set optimal directions of view. These can be defined relative to normal and tangential vectors on a plane that is fitted to the outline of a pathology segment and can then be stored in order to be retrieved later on during the interventional process. Hence, this method shortens the peri-operative phase and reduces the X-ray radiation exposure to the patient.

While the invention has been illustrated and described in detail in the drawings and foregoing description, such illustration and description are to be considered illustrative or exemplary and not restrictive; the invention is not limited to the disclosed embodiments.

LIST OF REFERENCE SIGNS

10 X-ray imaging system
12 X-ray radiation source
14 table
16 X-ray image detection module
18 calculation unit
20 display unit
22 interface unit
24 aorta
26 ostia
28 stent
30 reference plane
32 outline
34 center point
36 plane spanning point
38 normal vector
40 tangential vector
42 defining a plane
422 spanning reference plane
424 segmenting object
426 determining outline
428 spanning reference plane
44 defining a center
46 storing
48 registering
50 selecting
52 steering
54 conducting parallax compensation
542 generating sphere
544 determining intersection
56 optimal viewing direction vector
58 sphere
60 iso-center
62 X-ray detector
64 intersection
66 center of X-ray detector
68 point on X-ray detector

The invention claimed is:

1. A method for positioning an X-ray image acquisition device having an X-ray radiation source and an X-ray detector, the X-ray radiation source being capable of emitting X-ray radiation onto an object under an adjustable viewing direction depending on geometrical parameters of the X-ray image acquisition device, the method comprising the steps of:

creating a straight reference plane intersecting a three-dimensional representation of the object;

creating a center point as a geometrical center of an intersection area of the three-dimensional representation of the object on the reference plane;

creating (i) a normal vector and (ii) at least one tangential vector, wherein the normal vector is defined as a vector through the center point, extending perpendicularly to the reference plane, and wherein the at least one tangential vector is defined as a vector through the center point, extending tangentially on the reference plane;

defining at least one viewing direction derived from the normal vector and/or at least one tangential vector; and registering (i) the reference plane, (ii) the three-dimensional representation of the object's frame of reference and (iii) the X-ray image acquisition device's frame of reference; and adjusting the geometrical parameters of the X-ray image acquisition device according to at least one optimal viewing direction selected from the at least one defined viewing direction.

2. The method according to claim 1, wherein creating the reference plane comprises spanning the reference plane such that an average distance from trajectory points of the three-dimensional representation of the object to the reference plane are minimized.

3. The method according to claim 1, further comprising the step of:

segmenting the three-dimensional representation of the object into sub-volumes;

determining an outline of at least one segmented sub-volume; and spanning the reference plane such that an average distance from a trajectory defined by the outline of the at least one segmented sub-volume is minimized.

4. The method according to claim 1, further comprising the step of:
storing optimal viewing directions in a storage.

5. A data processing device for positioning an X-ray image acquisition device, the data processing device comprising a data processor, which is adapted for performing the method as set forth in claim 1, and
a storage means for storing and supplying the selected viewing directions.

6. A medical viewing system comprising a data processing device according to claim 5.

7. A non-transitory computer-readable medium on which there is stored a computer program for positioning an X-ray image acquisition device, the computer program, when being executed by a data processor, is adapted for controlling the method as set forth in claim 1.

8. A non-transitory computer-readable medium embodied with a computer program executable by a data processor for causing the data processor to position an X-ray image acquisition device according to the method of claim 1.

9. The method according to claim 1, further comprising conducting a parallax compensation by the steps of:
generating a sphere around a center of the X-ray image acquisition device, wherein a radius of the sphere equals a distance between the center of the X-ray image acquisition device and the X-ray radiation source;
determining an intersection between a straight line through the center point of the reference plane in a direction of an optimal viewing direction and the sphere; and
adjusting the geometry parameters of the X-ray image acquisition device to match the intersection and a focal spot of the X-ray source.

10. A method for positioning an X-ray image acquisition device having an X-ray radiation source and an X-ray detector, the X-ray radiation source being capable of emitting X-ray radiation onto an object under an adjustable viewing direction depending on geometrical parameters of the X-ray image acquisition device, the method comprising the steps of:
creating a straight reference plane intersecting a three-dimensional representation of the object;
creating a center point within an intersection area of the three-dimensional representation of the object on the reference plane;
creating a normal vector and at least one tangential vector within the reference plane;
defining at least one viewing direction derived from the normal vector and/or at least one tangential vector;
registering the reference plane, the three-dimensional representation of the object's frame of reference and the X-ray image acquisition device's frame of reference; and
adjusting the geometrical parameters of the X-ray image acquisition device, further comprising conducting a parallax compensation by the steps of:
generating a sphere around a center of the X-ray image acquisition device, wherein a radius of the sphere equals a distance between the center of the X-ray image acquisition device and the X-ray radiation source;
determining an intersection between a straight line through the center point of the reference plane in a direction of an optimal viewing direction and the sphere; and
adjusting the geometry parameters of the X-ray image acquisition device to match the intersection and a focal spot of the X-ray source.

11. The method according to claim 10, wherein creating the reference plane comprises spanning the reference plane such that an average distance from trajectory points of the three-dimensional representation of the object to the reference plane are minimized.

12. The method according to claim 10, further comprising the step of:
segmenting the three-dimensional representation of the object into sub-volumes;
determining an outline of at least one segmented sub-volume; and
spanning the reference plane such that an average distance from a trajectory defined by the outline of the at least one segmented sub-volume is minimized.

13. The method according to claim 10, further comprising the step of:
storing at least one optimal viewing direction in a storage, wherein the at least one optimal viewing direction is selected from the at least one defined viewing direction.

14. A data processing device for positioning an X-ray image acquisition device, the data processing device comprising a data processor, which is adapted for performing the method as set forth in claim 10, and
a storage for storing and supplying selected viewing directions.

15. A medical viewing system comprising a data processing device according to claim 14.

* * * * *